(12) United States Patent
Ducharme et al.

(10) Patent No.: US 9,042,964 B2
(45) Date of Patent: *May 26, 2015

(54) SYSTEM AND METHOD FOR FIDUCIAL DEPLOYMENT VIA SLOTTED NEEDLE

(75) Inventors: Richard W. Ducharme, Winston-Salem, NC (US); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 313 days.

This patent is subject to a terminal disclaimer.

(21) Appl. No.: 12/764,432

(22) Filed: Apr. 21, 2010

(65) Prior Publication Data

US 2010/0280367 A1 Nov. 4, 2010

Related U.S. Application Data

(60) Provisional application No. 61/174,196, filed on Apr. 30, 2009.

(51) Int. Cl.
*A61B 5/05* (2006.01)
*A61B 17/34* (2006.01)
*A61B 19/00* (2006.01)
(Continued)

(52) U.S. Cl.
CPC .............. *A61B 17/3468* (2013.01); *A61B 5/05* (2013.01); *A61B 1/018* (2013.01); *A61B 17/00234* (2013.01); *A61B 17/06166* (2013.01); *A61B 19/54* (2013.01); *A61B 2017/0417* (2013.01); *A61B 2019/5408* (2013.01); *A61B 2019/5425* (2013.01); *A61B 2019/5487* (2013.01);
(Continued)

(58) Field of Classification Search
CPC ................. A61B 2019/5487; A61B 17/06166; A61B 5/05; A61B 2019/5408; A61B 2019/5425; A61B 2019/5491; A61B 17/3468; A61B 17/00234; A61B 1/018; A61B 19/54; A61B 2017/0417; A61M 37/0069; A61N 5/1001; A61N 5/1049
USPC .......... 600/7, 407, 426, 427; 606/49, 116, 153
See application file for complete search history.

(56) References Cited

U.S. PATENT DOCUMENTS 2,009,393 A 7/1935 Faille
2,269,963 A 1/1942 Wappler
(Continued)

FOREIGN PATENT DOCUMENTS

EP 0093101 11/1983
EP 0093101 A2 11/1983
(Continued)

OTHER PUBLICATIONS

Marker Kit, "Gold fiducial markers—Accurate localization for soft tissue targets," Best Medical International, Inc., Springfield, VA, Jan. 2008, pp. 43-54.
(Continued)

*Primary Examiner* — Vani Gupta
(74) *Attorney, Agent, or Firm* — Brinks Gilson & Lione

(57) ABSTRACT

Embodiments include a fiducial deployment system and method for use thereof. A fiducial may include one or more protuberances configured to engage one or more slots in a needle of the system. The needle may be configured to deliver a plurality of fiducials to a target location in serial fashion, one at a time. In certain embodiments, echogenic placement of fiducials may present certain advantages.

15 Claims, 12 Drawing Sheets

(51) Int. Cl.
*A61M 37/00* (2006.01)
*A61B 1/018* (2006.01)
*A61B 17/00* (2006.01)
*A61B 17/06* (2006.01)
*A61B 17/04* (2006.01)
*A61N 5/10* (2006.01)

(52) U.S. Cl.
CPC .... *A61B2019/5491* (2013.01); *A61M 37/0069* (2013.01); *A61N 5/1001* (2013.01); *A61N 5/1049* (2013.01)

(56) References Cited

U.S. PATENT DOCUMENTS

| | | | |
|---|---|---|---|
| 2,620,796 | A | 12/1952 | Eriksen et al. |
| 3,470,834 | A | 10/1969 | Bone |
| 3,815,798 | A | 6/1974 | Lavitch et al. |
| 3,820,545 | A | 6/1974 | Jefferts |
| 4,086,914 | A | 5/1978 | Moore |
| 4,105,030 | A | 8/1978 | Kercso |
| 4,154,239 | A | 5/1979 | Turley |
| 4,451,254 | A | 5/1984 | Dinius et al. |
| 4,646,740 | A | 3/1987 | Peters et al. |
| 4,648,542 | A | 3/1987 | Fox et al. |
| 4,661,103 | A | 4/1987 | Harman |
| 4,700,692 | A | 10/1987 | Baumgartner |
| 4,716,901 | A | 1/1988 | Jackson et al. |
| 4,807,628 | A | 2/1989 | Peters et al. |
| 4,976,686 | A | 12/1990 | Ball et al. |
| 5,002,548 | A | 3/1991 | Campbell et al. |
| 5,024,727 | A | 6/1991 | Campbell et al. |
| 5,047,038 | A | 9/1991 | Peters et al. |
| 5,281,197 | A | 1/1994 | Arias et al. |
| 5,669,543 | A | 9/1997 | Ueno |
| 5,755,726 | A | 5/1998 | Pratt et al. |
| 5,810,769 | A | 9/1998 | Schlegel et al. |
| 5,860,909 | A | 1/1999 | Mick et al. |
| 6,004,320 | A | 12/1999 | Casscells et al. |
| 6,186,144 | B1 | 2/2001 | Davis et al. |
| 6,210,315 | B1 | 4/2001 | Andrews et al. |
| 6,220,248 | B1 | 4/2001 | Voegele et al. |
| 6,221,003 | B1 | 4/2001 | Sierocuk et al. |
| 6,228,055 | B1 | 5/2001 | Foerster et al. |
| 6,264,599 | B1 | 7/2001 | Slater et al. |
| 6,267,718 | B1 | 7/2001 | Vitali et al. |
| 6,283,948 | B1 | 9/2001 | McKernan et al. |
| 6,402,677 | B1 | 6/2002 | Jacobs |
| 6,450,938 | B1 | 9/2002 | Miller |
| 6,569,077 | B2 | 5/2003 | Schmidt |
| 6,592,508 | B1 | 7/2003 | Ravins et al. |
| 6,613,002 | B1 | 9/2003 | Clark et al. |
| 6,796,935 | B1 | 9/2004 | Savino |
| 6,824,507 | B2 | 11/2004 | Miller |
| 6,837,844 | B1 | 1/2005 | Ellard et al. |
| 6,889,833 | B2 | 5/2005 | Seiler et al. |
| 7,001,341 | B2 | 2/2006 | Gellman et al. |
| 7,008,368 | B2 | 3/2006 | Terwiliger et al. |
| 7,041,048 | B2 | 5/2006 | Drobnik et al. |
| 7,083,566 | B2 | 8/2006 | Tornes et al. |
| 7,104,945 | B2 | 9/2006 | Miller |
| 7,144,386 | B2 | 12/2006 | Korkor et al. |
| 7,280,865 | B2 | 10/2007 | Adler |
| 7,335,155 | B2 | 2/2008 | Chu |
| 7,361,135 | B2 | 4/2008 | Drobnik et al. |
| 7,429,240 | B2 | 9/2008 | Miller |
| 7,465,279 | B2 | 12/2008 | Beckman et al. |
| 7,565,191 | B2 | 7/2009 | Burbank et al. |
| 7,577,473 | B2 | 8/2009 | Davis et al. |
| 7,588,528 | B2 | 9/2009 | Drobnik et al. |
| 7,615,076 | B2 | 11/2009 | Cauthen, III et al. |
| 7,651,505 | B2 | 1/2010 | Lubock et al. |
| 7,656,191 | B2 | 2/2010 | Lewis et al. |
| 7,736,343 | B2 | 6/2010 | Marshall et al. |
| 7,819,820 | B2 | 10/2010 | Field et al. |
| 7,850,639 | B2 | 12/2010 | Rue et al. |
| 2003/0120141 | A1 | 6/2003 | Adler |
| 2003/0233101 | A1 | 12/2003 | Lubock et al. |
| 2003/0233126 | A1 | 12/2003 | Kaplan et al. |
| 2004/0097780 | A1 | 5/2004 | Otsuka |
| 2004/0236213 | A1 | 11/2004 | Jones et al. |
| 2004/0260199 | A1 | 12/2004 | Hardia et al. |
| 2005/0038355 | A1 | 2/2005 | Geliman et al. |
| 2005/0267319 | A1 | 12/2005 | White et al. |
| 2006/0058569 | A1 | 3/2006 | Chu |
| 2006/0173236 | A1 | 8/2006 | White et al. |
| 2006/0235298 | A1 | 10/2006 | Kotmel et al. |
| 2007/0167736 | A1 | 7/2007 | Dietz et al. |
| 2007/0270640 | A1 | 11/2007 | Dimitriou et al. |
| 2008/0033280 | A1 | 2/2008 | Lubock et al. |
| 2008/0033286 | A1 | 2/2008 | Whitmore et al. |
| 2008/0243148 | A1* | 10/2008 | Mikkaichi et al. ............ 606/144 |
| 2008/0269688 | A1 | 10/2008 | Colucci et al. |
| 2008/0287782 | A1 | 11/2008 | Traboulsi et al. |
| 2009/0105584 | A1* | 4/2009 | Jones ............................ 600/431 |
| 2009/0131734 | A1 | 5/2009 | Neustadter et al. |
| 2009/0209804 | A1 | 8/2009 | Seiler et al. |
| 2010/0010342 | A1 | 1/2010 | Burbank et al. |
| 2010/0036241 | A1 | 2/2010 | Mayse et al. |
| 2010/0063392 | A1* | 3/2010 | Nishina et al. ................ 600/439 |
| 2010/0137891 | A1 | 6/2010 | Shalon et al. |
| 2010/0280367 | A1 | 11/2010 | Ducharme et al. |
| 2010/0331677 | A1 | 12/2010 | Hong et al. |
| 2011/0028831 | A1 | 2/2011 | Kent |
| 2011/0071424 | A1 | 3/2011 | Nock et al. |
| 2011/0152611 | A1 | 6/2011 | Ducharme et al. |
| 2013/0006101 | A1 | 1/2013 | McHugo et al. |
| 2013/0006286 | A1 | 1/2013 | Lavelle et al. |
| 2013/0096427 | A1 | 4/2013 | Murray et al. |

FOREIGN PATENT DOCUMENTS

| | | |
|---|---|---|
| EP | 1518549 | 3/2005 |
| FR | 2 762 517 A1 | 4/1997 |
| FR | 2762517 | 4/1997 |
| JP | 6323312 | 11/1994 |
| JP | 6323312 A | 11/1994 |
| WO | WO9719724 | 6/1997 |
| WO | WO0100101 | 1/2001 |
| WO | WO2007094001 | 8/2007 |
| WO | WO2007103204 | 9/2007 |
| WO | WO2009100106 | 8/2009 |
| WO | WO2009132349 | 10/2009 |
| WO | WO2010126750 | 11/2010 |

OTHER PUBLICATIONS

PCT Notification of Transmittal of the International Search Report and the Written Opinion of the International Searching Authority, or the Declaration for PCT Application No. PCT/US2010/031842, date of mailing Nov. 3, 2010.

Ammar et al., "Fiducial placement for sterotactic radiation by using EUS feasibility when using a marker compatible with a standard 22-gauge needle," Gastrointestinal Endoscopy, vol. 71, No. 3, pp. 630-633, www.giejournal.org, St. Louis, MO 20210.

Classen et al. "Gastroenterological Endoscopy," EUS-Guided Implantation of Radiopaque Markers (Fiducials), p. 475.

DiMaio et al., "EUS-guided fiducial placement for image-guided radiation therapy in GI malignancies by using a 22-gauge needle (with videos)," Gastrointestinal Endoscopy, vol. 71, No. 7, pp. 1204-1210.

International Search Report for International Application No. PCT/US2010/059641, dated mailed May 25, 2011, 7 pages.

PCT Notification of Transmittal of the International Search Report and Written Opinion of the International Search Authority, or the Declaration for PCT Application No. PCT/US2010/031842, date of mailing May 6, 2010.

International Search Report for International Application No. PCT/US2012/058679, dated Jan. 2, 2013, 3 pages.

International Search Report for International Application No. PCT/US2013/023401, dated May 7, 2013, 2 pages.

* cited by examiner

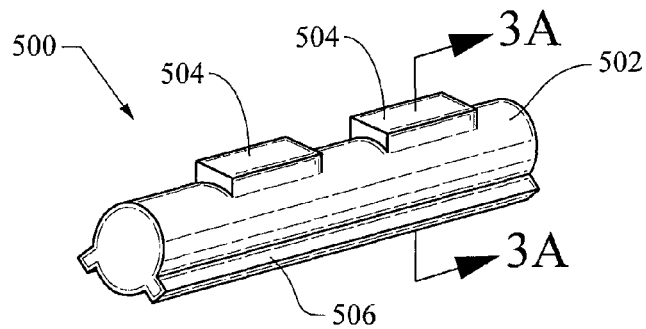
FIG. 3
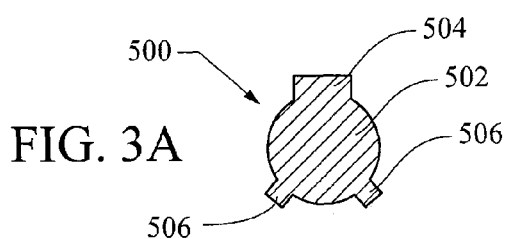
FIG. 3A
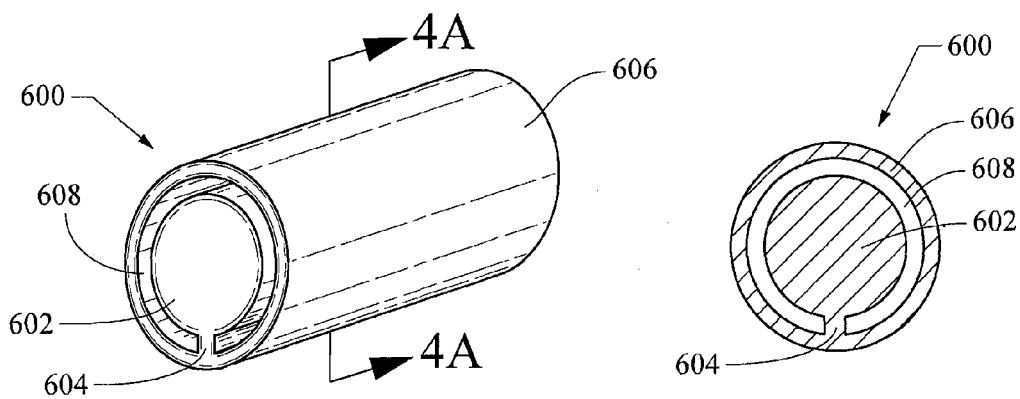
FIG. 4
FIG. 4A
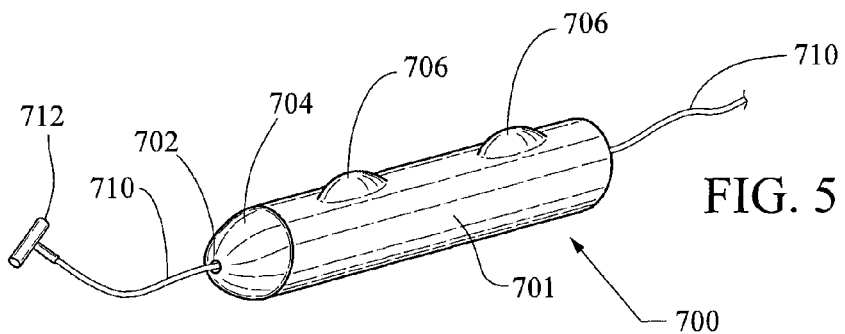
FIG. 5

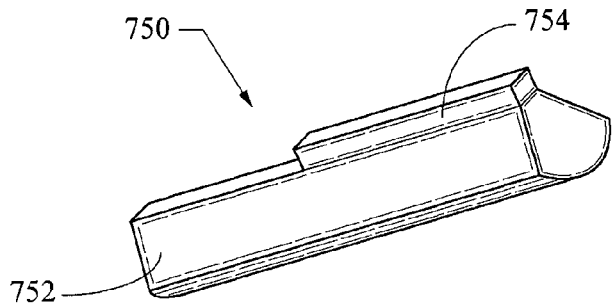
FIG. 6
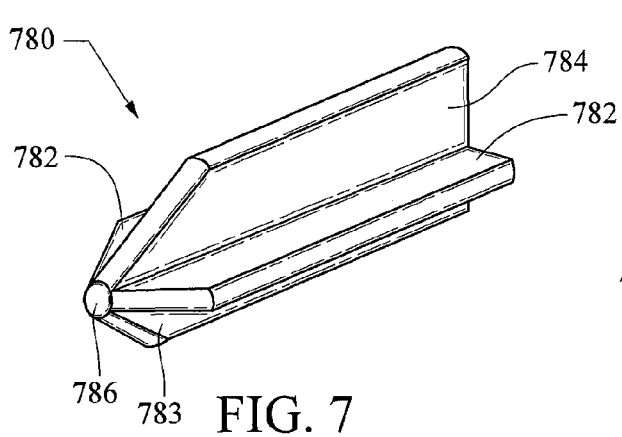 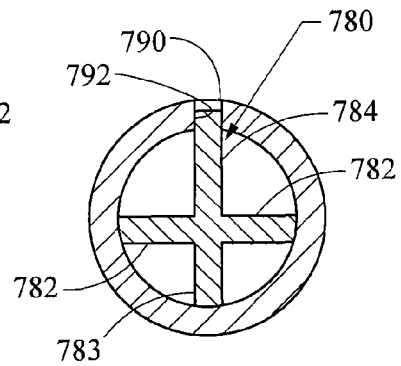
FIG. 7　　　　　　　FIG. 7A
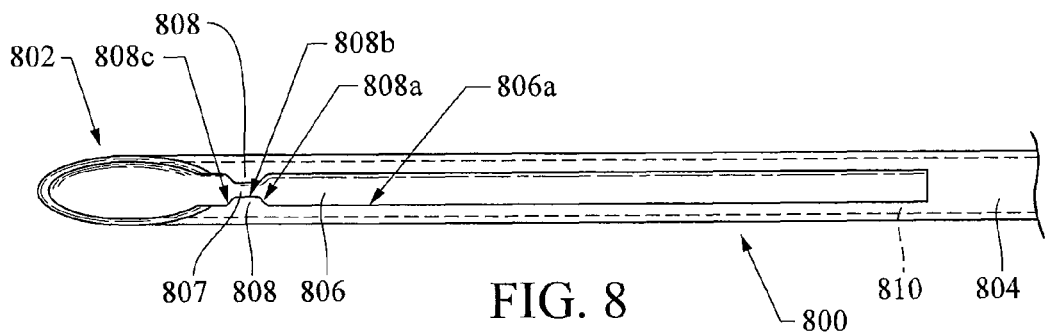
FIG. 8
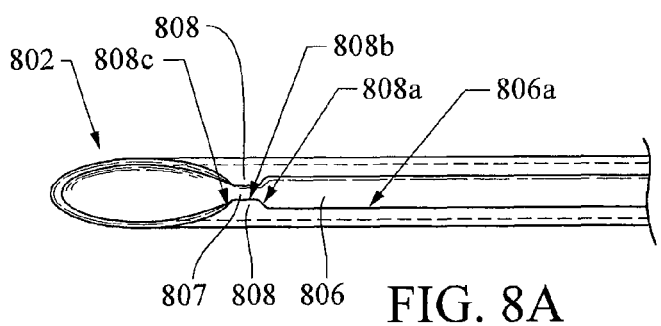 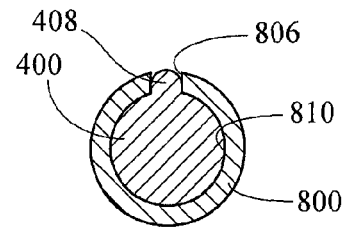
FIG. 8A　　　　　　FIG. 9

SYSTEM AND METHOD FOR FIDUCIAL DEPLOYMENT VIA SLOTTED NEEDLE

RELATED APPLICATIONS

The present patent document claims the benefit of the filing date of Provisional U.S. Patent Application Ser. No. 61/174,196, filed April 30, 2009, which is incorporated herein by reference.

TECHNICAL FIELD

The invention relates generally to a medical device system including one or more fiducials and methods of use for same. More particularly, the invention pertains to specially-configured fiducials, needles configured for use with them, and methods of use for same.

BACKGROUND

Medical procedures often require locating and treating target areas within a patient. Focused, dose-delivery radiation therapy requires locating the target with a high degree of precision to limit damaging healthy tissue around the target. It is particularly important to know or estimate the precise location of the target in radiation oncology because it is desirable to limit the exposure of adjacent body parts to the radiation in a patient already suffering the depredations of cancer. However, in all treatment procedures, whether radiologic or otherwise, it is most desirable to be able to accurately target a region to be treated.

In many applications, it is not possible to directly view a treatment target or portion thereof (such as, for example, a cancerous tumor, cyst, pseudocyst, or other target) that needs to be acted on in some manner. As one example, when treating a lung or pancreatic tumor with radiation, it may not possible to view the actual tumor within the patient immediately before the radiation treatment. It is therefore highly advantageous to have some mechanism for permitting the tumor to be located accurately so that the radiation treatment can be targeted at the tumor while avoiding damage to healthy tissue.

Even for target regions that may be visualized using CAT (computer-assisted tomography) scans, MRI (magnetic resonance imaging), x-rays, ultrasound, or other techniques, difficulties often arise in targeting a treatment. This is particularly true for target regions within a torso of a patient and soft tissue regions. Due to the mobility of tissues in those regions (e.g., movement of internal organs during respiration, the movement with a patient's movements/change of body position of breast tissue), a target region may not remain fixed relative to anatomical landmarks and/or to marks that can be placed onto an external surface of a patient's body during one of those visualization procedures.

Several techniques have been developed to address this problem. One such technique is to place markers into the patient along the margins of the target region. The markers may be active (e.g., emitting some kind of signal useful in targeting a therapy) or passive (e.g., non-ferromagnetic gold markers—called fiducials—that can be used for targeting under ultrasound, MRI, x-ray, or other targeting techniques, which may be included in a treatment device).

A fiducial is typically formed of a radio-opaque material that the target can be effectively located and treated with a device that targets a site using the fiducials as positional markers under radiographic detection. Typically, the fiducials may be inserted into the patient during a simple operation. Percutaneous placement is most commonly used. However, use of minimally-invasive placement via an endoscope has recently developed for fiducial placement into a patient's internal organs. For example, percutaneous placement of fiducials along the margins of a pancreatic tumor can be complex and painful (particularly for obese patients, where the needle size is necessarily larger). Another process using percutaneously implanted objects in a patient is brachytherapy. In brachytherapy, radioactive sources or "seeds" are implanted into and/or adjacent a tumor to provide a high dose of radiation to the tumor, but not the healthy tissue surrounding the tumor.

FIGS. 1A and 1B show longitudinal sectional views of a two-piece introducer 100 of the prior art useful for placement of brachytherapy seeds or fiducials. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a bevel-tipped cannula 108 extending through the second handle 103. The cannula 108 is configured to hold a seed/fiducial 110. The cannula 108 has a distal tip 105 configured for percutaneous implantation of the seed/fiducial 110 into the patient.

In a "pre-loaded configuration," the seed/fiducial 110 is retained in the cannula 108 by a plug 112 made from bone wax or other suitable bio-compatible material(s). This is typically accomplished by a "muzzle-loading" technique where the fiducial is placed into the distal needle and then held in place by the bone wax plug. This can present some challenges, as the bone wax plug 112 can be visible as an artifact in the patient, potentially interfering with clear visualization of body structures or treatment devices. With this configuration, the cannula 108 must be withdrawn and reloaded after delivery of each seed/fiducial 110. If the target locations for the fiducials are very far apart, use of a single percutaneous introducer cannula/trocar for multiple introductions of the cannula 108 may not be possible. In such a circumstance, the patient must endure several percutaneous punctures (and the increased attendant risk of infection for each).

To implant the desired arrangement of seeds/fiducials 110 at a target location in a patient, an operator pushes the cannula 108 in a first direction (arrow A) to insert the tip 105 into the patient (typically under fluoroscopic visualization). The operator then pushes the second handle 103 further in the first direction to position the tip 105 at the desired depth within the patient where a seed/fiducial 110 is to be implanted. Throughout this motion, the operator moves the needle 102 and the stylet 104 together as a unit. At the desired depth/location, the operator grasps the first handle 101 with one hand and the second handle 103 with the other hand. Then, the operator holds the first handle 101 stationary while simultaneously sliding the second handle 103 back in a second direction (arrow B) toward the first handle 101. As shown in FIG. 1B, this movement causes the cannula 108 to retract over the seed/fiducial 110 to implant it in the patient. Alternatively, the operator may move the first handle 101 in the first direction (arrow A) while sliding the second handle 103 back in the second direction (arrow B). This causes the stylet 104 to push the seeds 110 out of the cannula 108. The procedure is then repeated to place other seeds/fiducials 110. When being used for targeting of radiation therapy, a minimum of three fiducials is typically required.

As will be appreciated from the disclosed structure, after deploying one fiducial one may alternatively reload the introducer 100 from the proximal end by completely withdrawing the stylet 104, then placing another fiducial into the needle lumen and advancing it therethrough to a second location to which the distal needle tip 105 has been directed (a "breech-loading" technique). Provided that the fiducial target sites are sufficiently close together to allow this technique, it can reduce the number of percutaneous punctures needed to place more than one fiducial. However, it creates a problem for procedures where ultrasound is being used or is to be used in the near-future because it introduces air pockets into the tissue and related fluids. Those air pockets with tissue and/or fluid are echogenic in a manner that can interfere with ultrasound visualization of a target area and/or tools being used to diagnose or treat in/around the area. In some brachytherapy techniques, a series of fiducials may be preloaded into the needle—either separately or connected by a suture or similar device—then placed together in fairly close proximity; however, such a technique typically is not effective for placing three or more fiducials in sufficiently disparate locations to use for targeting a treatment relative to, for example, margins of a tumor.

The process is similar when implemented endoscopically in the manner developed rather recently, except that the needle and stylet are of the type known in the art for use through the working channel of an endoscope. One limitation of current endoscopic techniques is the size of fiducial that can be introduced. With the size limitation of endoscope working channels, the largest needle that can typically be used without risking bending, crimping, curving or otherwise damaging a needle (that does not have an internal stylet or other support) during advancement out of the endoscope to an anatomical target is a 19-gauge needle. This limits the size of the fiducial that can be introduced through the needle lumen using current, cylindrical fiducials. The endoscopic technique generally suffers from the same reloading problems as described above. Even though the percutaneous punctures are not an issue, having to withdraw and reload takes up valuable time and complicates the procedure, potentially requiring additional personnel, whether only the stylet is withdrawn for "breech-loading" or the entire device is withdrawn for "muzzle-loading."

It would be desirable to use ultrasound, and particularly endoscopic ultrasound (EUS) for navigation and placement of fiducials. As such it would be desirable to provide and use the largest possible fiducial that will provide improved echogenicity based on its size and echogenic profile. It would be desirable to provide multiple fiducials in a needle that can be introduced in a controlled serial manner (one at a time) rather than requiring manual reloading after placement of each fiducial.

BRIEF SUMMARY

Embodiments of a fiducial deployment system described herein may include one or more of: one or a plurality of fiducials having one or more protuberances, a slotted needle configured for delivering a plurality of fiducials in serial fashion, and a method of delivering fiducials to a target region.

BRIEF DESCRIPTION OF THE DRAWINGS

FIGS. 3-3A show, respectively, a top perspective view and a transverse section view of a fourth embodiment of a fiducial;

FIGS. 4-4A show, respectively, a top perspective view and a transverse section view of a fifth embodiment of a fiducial;

FIG. 5 shows a sixth fiducial embodiment, including a suture along which the fiducial is slidably disposed;

FIG. 6 shows a seventh fiducial embodiment;

FIGS. 7-7A show, respectively, a top perspective view and a transverse section view of an eighth embodiment of a fiducial;

FIG. 8 shows a top view of a slotted needle embodiment;

FIG. 9 shows a transverse section view of the needle of FIG. 8, with a fiducial disposed in its lumen;

DETAILED DESCRIPTION

As used herein, the terms "proximal" and "distal" are used in the common usage sense wherein they refer respectively to a handle/doctor-end of a device or related object and a tool/patient-end of a device or related object.

Figure 1A:
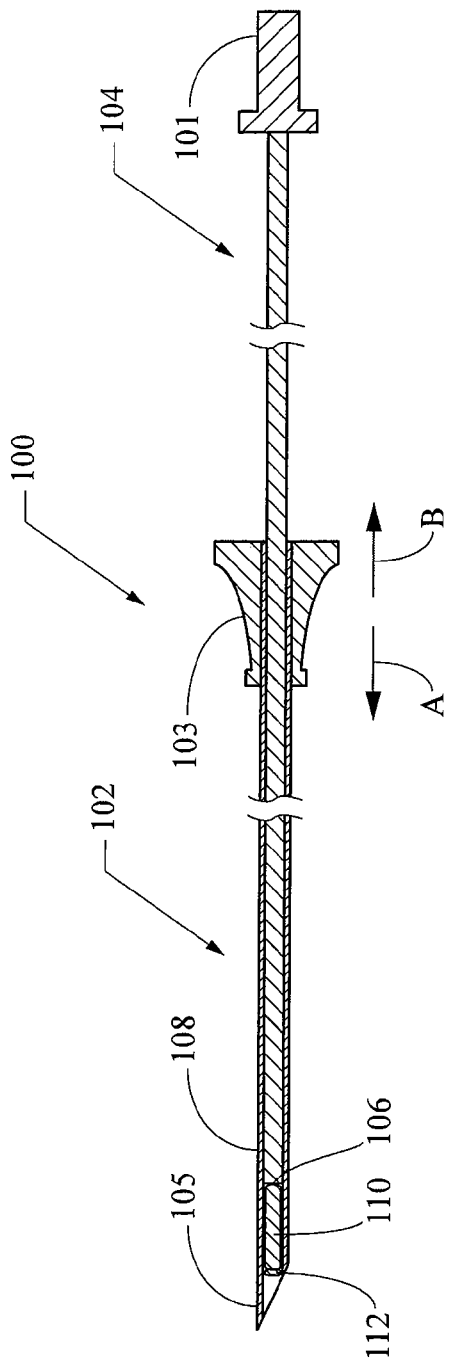
FIGS. 1A-1B show a prior art fiducial introducer and method of use.
Figure 1B:
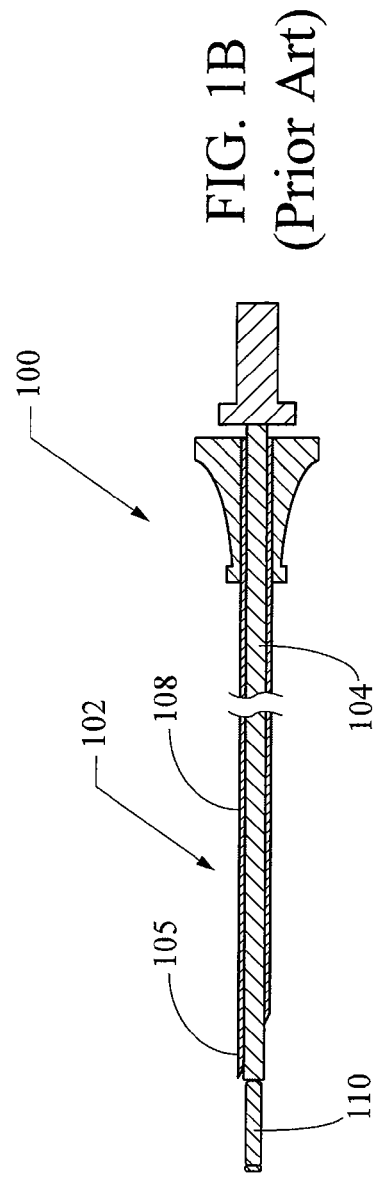
Figure 2A:
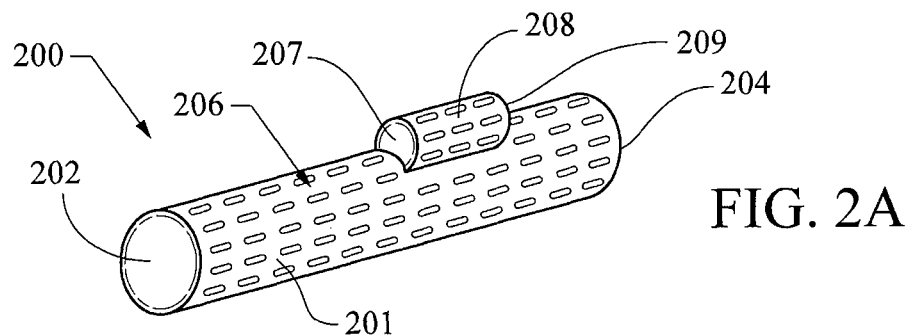
FIG. 2A shows a first embodiment of a fiducial.

Referring to FIG. 2A, a first embodiment of a fiducial 200 is described. The fiducial is configured for deployment in a patient body to be used for demarcating an internal body site (and, a fiducial may also be configured for use in brachytherapy within the scope of the present invention). The fiducial 200 has a generally columnar body that is generally cylindrical with a generally circular transverse cross-section. A longitudinal surface face 206 of the body is shown as being dimpled to enhance its ability to reflect ultrasound waves and thereby provide a desirable echogenic profile. This dimpled characteristic may alternatively be embodied as a different irregular, patterned, or textured surface feature (e.g., knurled, ribbed) that may enhance the echogenicity of the fiducial 200, which will aid in visualizing it during EUS-guided placement, and allow it to be used in ultrasound visualization of a target site being marked by one or more fiducials 200 (e.g., a tumor). The fiducial 200 preferably will be formed of a radio-opaque, non-ferromagnetic material such as, for example, gold, platinum, palladium, iridium, or alloys thereof, with one preferred embodiment including an alloy of palladium with rhenium (advantages of which include desirable radio-opacity, market-price stability superior to gold, and ultrasound-reflectivity/echogenicity due to density). Being radio-opaque will allow the fiducial to be used in deployment techniques using fluoroscopy, as well as making it detectable/visualizable by radiographic means during a treatment or other procedure where it may be desirable to know the location(s) of one or more fiducials. Being non-ferromagnetic will lessen the likelihood that visualization techniques or other procedures employing magnetic fields such as, for example, MRI, will re-orient or otherwise dislodge a fiducial. Echogenic construction of a fiducial or needle may be enhanced by surface texture, but can also be provided by structural inclusions such as embedded bubbles or beads that provide for a different ultrasound reflectivity than material surrounding them.

A protuberance 208 projects from the longitudinal face 206 of the fiducial body 201. The protuberance 208 has a distal protuberance end 207 corresponding to a distal body end 202, and proximal protuberance end 209 corresponding to a proximal body end 204. The distal and proximal body ends 202, 204 are each generally planar and transverse to the longitudinal axis. In this embodiment, the protuberance 208 is rounded and substantially parallel to the longitudinal central axis of the fiducial body, is only about one-half the length of the body 201, and is longitudinally located nearer the proximal end 204 than the distal end 204 of the body. In a preferred embodiment, the fiducial 200 is configured and dimensioned for passage through and release from a needle lumen. For an endoscopic delivery system, the fiducial body 201 (exclusive of the protuberance) preferably will have an outer diameter (OD) of about the same or less than the inner diameter (ID) of a needle lumen, but the OD of the fiducial body preferably will be no greater than the needle ID. As used herein, the OD of the fiducial refers to an imaginary circle (or other geometric shape) whose outermost boundaries all fit within the ID of the needle lumen. In other words, it is preferable that the fiducial is dimensioned to fit slidably into the needle lumen, except the protuberance, which projects into the slot.

The longer body portion distal of the protuberance can help make certain that, during deployment through a needle, a first fiducial distal of this second fiducial will be fully advanced out of the needle before this one is positioned for deployment, as will be made clearer with reference to FIGS. 7-11C below. Accordingly, in many preferred embodiments, the fiducial protuberance (of the second and successive fiducials) will be nearer its proximal end than its distal end, so that the distal fiducial body portion projects sufficiently distally that it will advance the preceding first fiducial completely out of the needle lumen by the time that the second fiducial is in a position to be deployed (see FIGS. 10-10A and corresponding text). It should be appreciated that, even if all surfaces of the central fiducial portion 201 and protuberance 208 are generally smooth, the preferred materials forming the fiducial 200 and the presence of the protuberance 208 may provide a desirable echogenic profile that is readily visualizable under ultrasound at a resolution sufficient for locating and/or navigating it in a patient's body.

Figure 2B:
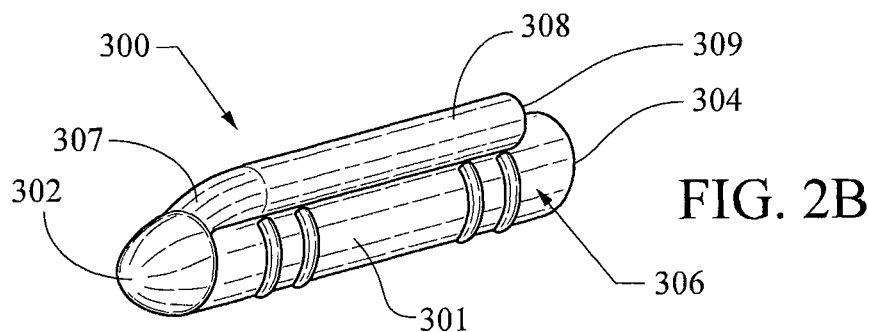
FIG. 2B shows a second embodiment of a fiducial.

FIG. 2B shows another embodiment of a fiducial 300. The fiducial 300 has a generally cylindrical body with a generally circular transverse cross-section. A longitudinal surface face 306 of the body 301 is shown as being ridged to enhance its ability to reflect ultrasound waves and thereby provide a desirable echogenic profile. This ridged characteristic may alternatively be embodied as a different non-smoothly-cylindrical or otherwise patterned surface feature (e.g., knurled, ribbed) that will enhance the echogenicity of the fiducial 300, which will aid in visualizing it during EUS-guided placement, and allow it to be used in ultrasound visualization of a target site being marked by one or more fiducials 300 (e.g., a tumor).

A protuberance 308 projects from the longitudinal face 306 of the fiducial body. The protuberance 308 has a distal protuberance end 307 that tapers down to a rounded distal body end 302, and proximal protuberance end 309 corresponding to a generally planar proximal body end 304. In this embodiment, the protuberance 308 is rounded and substantially parallel to the longitudinal central axis of the fiducial body, and it is about the same length as the body. In a preferred embodiment, the fiducial 300 is configured and dimensioned for passage through and release from a needle lumen. For an endoscopic delivery system, the fiducial body (exclusive of the protuberance) will have an outer diameter (OD) of about the same or less than the inner diameter (ID) of a needle lumen, but the fiducial body OD preferably will be no greater than the needle ID.

Figure 2C:
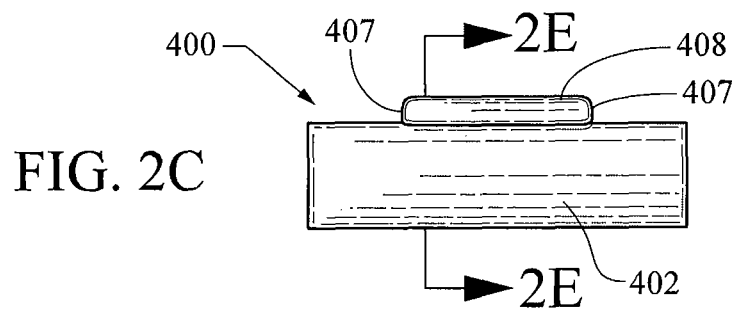
FIG. 2C-E show a third embodiment of a fiducial from, respectively, top, side, and transverse section views.
Figure 2D:
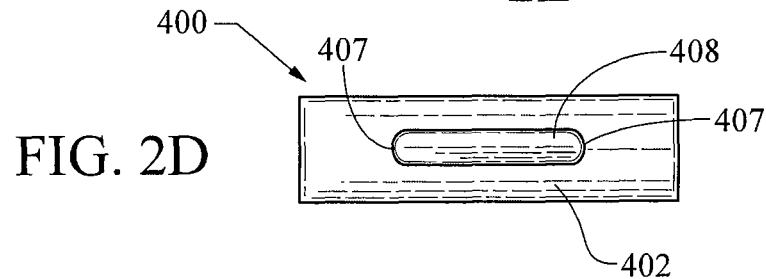
Figure 2E:
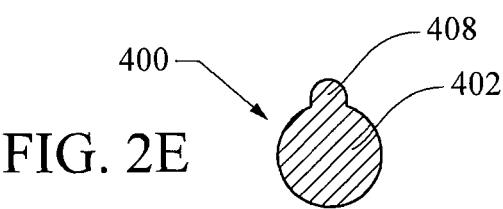

FIGS. 2C-2E show another embodiment of a fiducial 400. The fiducial 400 has a generally cylindrical body 402 formed as a mass with a generally circular transverse cross-section along its proximal and distal end sections. A protuberance 408 projects from the longitudinal circumferential face 406 of the fiducial body 402. As viewed from the top (shown in FIG. 2D), the protuberance 408 is generally obround. The irregular shape and increased surface area (as compared to a typical cylindrical fiducial) preferably enhances the echogenicity of the fiducial, which preferably is already desirable due in part to its composition.

The protuberance 408 has a protuberance end faces 407 that may provide one or more of chamfered, filleted, and radiused transition to the outer face 406 of the body 402. The body 402 is generally a right cylinder, but for the protuberance 408. In this embodiment, the protuberance 408 is rounded and substantially parallel to the longitudinal central axis of the fiducial body, and it is about one half the length of the body 402, and it is centered along the body length. In a preferred embodiment, the fiducial 400 is configured and dimensioned for passage through and release from a needle lumen. For an endoscopic delivery system, the fiducial body (exclusive of the protuberance) will have an outer diameter (OD) of about the same or less than the inner diameter (ID) of a needle lumen, but the fiducial body OD preferably will be no greater than the needle ID.

An exemplary embodiment is also described with reference to FIGS. 2C-2D. In one exemplary embodiment the body 402 is about 0.12 inches (3.05 mm) long and has an OD of about 0.034 inches (0.86 mm). The protuberance 408 is about 0.06 inches (1.5 mm) long and is aligned along a midline of the body. The protuberance 408 projects about 0.008 inches (0.2 mm) above the OD of the body 402 and is about 0.011 inches (0.28 mm) wide. These measurements and proportions may be varied in other embodiments while remaining within the scope of the presently-claimed material. For example, the protuberance may me more distally or proximally located, and may be at an angle relative to the midline such that it partially spirals around the outer surface of the body. In certain preferred embodiments, the protuberance may be disposed at the proximal end of the fiducial, such that a distal fiducial body portion projects therefrom (see, e.g., the relative position of protuberance 754 in FIG. 6). As will be understood from FIGS. 8-10A, this configuration will provide for the leading/distal body portion of a second fiducial to push a first, more distal, fiducial as far distally as possible before the protuberance of the second fiducial engages tabs, cambered surfaces, or other distal fiducial-retention structures of a needle.

FIG. 2E shows an end view of a transverse section taken along line 2E-2E of FIG. 2C. It shows one embodiment of general proportions of a fiducial body and protuberance of the present system.

FIG. 3 shows an embodiment of a fiducial 500 that includes a plurality of protuberances. The fiducial 500 has a generally cylindrical body 502 with first and second parallel long protuberances 504 that extend most of the length of the body 500. The fiducial 500 also includes third and fourth short protuberances 506 that are longitudinally aligned with each other along the longitudinal axis of the body 502 and are also parallel with the ridge protuberances 504. As shown more clearly in FIG. 3A, which is a transverse section view along line 3A-3A of FIG. 3, the centerlines of the protuberances 504, 506 are shown as being generally equidistant (at about 60° from each other). It should be appreciated that the particular shapes, surface positions on fiducial bodies, and general proportions of these and the other protuberances disclosed herein may be interchanged or otherwise modified within the scope of the claims.

FIGS. 4 and 4A show another embodiment of a fiducial 600 that includes a generally cylindrical central body 602, a protuberance 604, and a columnar outer body 606 circumferentially encompassing most of the central body 602 in a manner forming a needle lumen 608. The protuberance connects the central body 602 to the outer body 606. FIG. 4A shows a transverse section view of the fiducial 600 along line 4A-4A of FIG. 4.

FIG. 5 shows a bullet-shaped fiducial 700 with a central fiducial lumen 702 extending longitudinally through its body 701. A suture 710 extends through the fiducial lumen 702 and terminates distally in a T-anchor 712. The distal end of the fiducial body 701 is rounded, forming a distal bullet-like nose 704. The surface of the fiducial 700 includes a pair of domed protuberances 706.

The embodiments described above each include a body formed as a generally longitudinal central fiducial portion that is generally cylindrical. However, it should be appreciated that other fiducial embodiments may include a main body that is non-cylindrical, or that includes both cylindrical and non-cylindrical portions. FIG. 6 shows an embodiment of a non-cylindrical fiducial 750. The fiducial 750 includes a generally columnar body portion 752 with a generally round-based-triangular transverse cross section. It has a generally parallelepiped protuberance 754 along one surface. Its generally flat planar surfaces may provide a desirable echogenic profile, which may be enhanced by texturing (e.g., knurling, dimpling, ridging, or another feature) of the surface.

FIGS. 7 and 7A show another embodiment of a non-cylindrical fiducial 780. As is shown most clearly in the transverse section view of FIG. 7A, the fiducial 780 has a generally columnar body having a t-shaped cross-section with four protuberances. Two generally symmetrical protuberances 782 each have about the same dimensions—extending about the same distance from a central longitudinal axis, with a third protuberance 783 extending downward between them. The tip-edge of each preferably is at least slightly rounded to complement the outer curvature of a needle when placed therein. The fourth protuberance 784 preferably is taller (i.e., projects further from the central longitudinal axis) than the other three. The distal end 786 of the fiducial 780 is shown with a tapered geometry that may terminate in a sharp point or a rounded tip.

The transverse section view of FIG. 7A shows one way that the fiducial 780 may be used with a needle of the present system (e.g., with a needle 800 described below with reference to FIG. 8). The fiducial 780 is disposed slidably removably in the needle lumen. The fourth protuberance 784 extends into a needle slot embodied as a groove 792, and the difference between the height of the fourth protuberance 782 and the height of the symmetrical protuberances 782 (each measured from a center longitudinal axis of the fiducial 780) preferably is slightly less than the thickness of the wall of the cannula 790. The shorter protuberances preferably fit within the inner diameter of the needle lumen, and it is generally desirable that one or more of them contacts the needle lumen to keep the fiducial 780 aligned in the lumen, as well as to provide maximum surface area for desirable echogenicity. It should be appreciated that modified versions of this embodiment may be practiced within the scope of the present invention as defined by the claims. For example, it will be appreciated that two or more than three protuberances may be used. Likewise, one or more of the protuberances may extend less than a full length of the fiducial and/or may be interrupted with one or more spaces along its length. The relative height of the protuberances may be varied along the length of various embodiments and/or within a single embodiment such that the heights of one or more protuberances are asymmetrical. Generally, it will be preferable for using this embodiment with a grooved needle that a groove-engaging protuberance extend further from a central longitudinal axis than all other protuberances.

FIG. 8 shows an embodiment of a fiducial introduction needle 800. The needle 800 is illustrated with a beveled distal tip 802. Its tubular cannula body 804 includes a longitudinal needle slot 806 along a distal end region of the cannula 804. The slot 806 preferably includes at least one detent including at least one detent surface, and more preferably two detents. The slot 806 is shown as being open through the entire wall of the cannula 804, but it should be appreciated that the slot may extend less than the thickness of the needle wall, such that it is embodied as a groove. In the embodiment of FIG. 8, the detent is formed as a narrowed portion 807 of the slot 806 between two tabs 808. The tabs 808 are generally trapezoidal, but may have a different geometry in other embodiments. Each of the transitions between the edge 806a of the needle slot 806, the proximal tab edge 808a, central tab edge 808b, and distal tab edge 808c may be cornered (e.g., chamfered or filleted) or rounded (e.g., radiused). The tabs 808 preferably are near the distal end of the slot 806. The cannula 804 generally circumferentially defines a needle lumen 810 configured to allow sliding passage therethrough of a fiducial such as, for example, a fiducial (e.g., those shown in FIGS. 2A-2D or others that would readily pass through the needle lumen 810, preferably with controllable retention of the fiducial(s) by the tabs 808). The needle may be constructed from a nickel-titanium alloy, cobalt-chromium (CoCr) alloy, stainless steel or any other suitable material. Its tip may have a different geometry than the beveled configuration shown. In an alternative embodiment, the tabs 808 may meet such that they will be forced to flex upward and/or outward to a greater degree to allow passage of a protuberance on a fiducial. And, the outer surface of the needle may be dimpled or otherwise textured to provide enhanced echogenicity.

An exemplary needle embodiment is also described with reference to FIG. 8, which exemplary needle embodiment may be configured and dimensioned for use with the exemplary fiducial needle embodiment described above with reference to FIGS. 2C-2D. In the exemplary needle embodiment, the ID of the needle lumen is at least about 0.034 inches (0.86 mm). The OD of the needle is about 0.042 inches (1.07 mm; about 19-gauge), with a wall-thickness of about 0.008 inches (0.2 mm). The slot portion proximal of the tabs is about 0.02 inches (0.5 mm) wide and about 0.42 inches (about 10.7 mm) long. Each of the tabs extends about 0.06 inches (0.15 mm) out of the slot edge and has a slot-facing edge that is about 0.02 inches (0.5 mm) long (not including the proximal and distal angled transitions from the slot edge, which are radiused at about 0.005 inches (0.13 mm)). These measurements and proportions may be varied in other embodiments, including those illustrated herein, while remaining within the scope of the presently-claimed material.

FIG. 9 shows a transverse section end view of a section of a needle 800 (as in FIG. 8) and a fiducial 400 (as in FIGS. 2C-2D). This view shows the preferred close tolerances and a preferred orientation of the fiducial body relative to the needle lumen 810 and the protuberance 408 relative to the needle slot 806.

A fiducial deployment system 1000 is described with reference to FIG. 10, which is an external view, and FIG. 10A which is a longitudinal section view taken along line 10A-10A of FIG. 10, using the needle 800 and fiducial 400 described above. The system 1000 includes a flexible elongate needle sheath 1002. The needle 800, including a more flexible proximal body portion 820 extends through a sheath lumen 1004. At least one fiducial 400, illustrated here as a plurality of fiducials 400, is disposed slidably removably in a distal region of the needle lumen 810 of the needle's cannular body. The central longitudinal body portion 402 substantially occupies the inner diameter of the needle lumen 810. The protuberance 408 of each fiducial 400 has a height that is about the same as the thickness of the needle wall, including the slot 806 into which the protuberances 408 project.

The protuberance 408 of the distal-most fiducial 400 is captured against the tabs 808 of the needle 800. A stylet 1006 configured for use as a pusher is disposed through a portion of the needle lumen 810 and preferably is configured for actuation from the proximal end, whereby it can be used to distally advance/push out the fiducials and/or hold them in place as the needle is withdrawn from around them. The presence of the fiducials and stylet in the needle 800 preferably improve its columnar strength reduce the likelihood that it will get bent, crimped, or otherwise damaged as it is navigated through and out of the distal end of an endoscope working channel (not shown).

Figure 10:
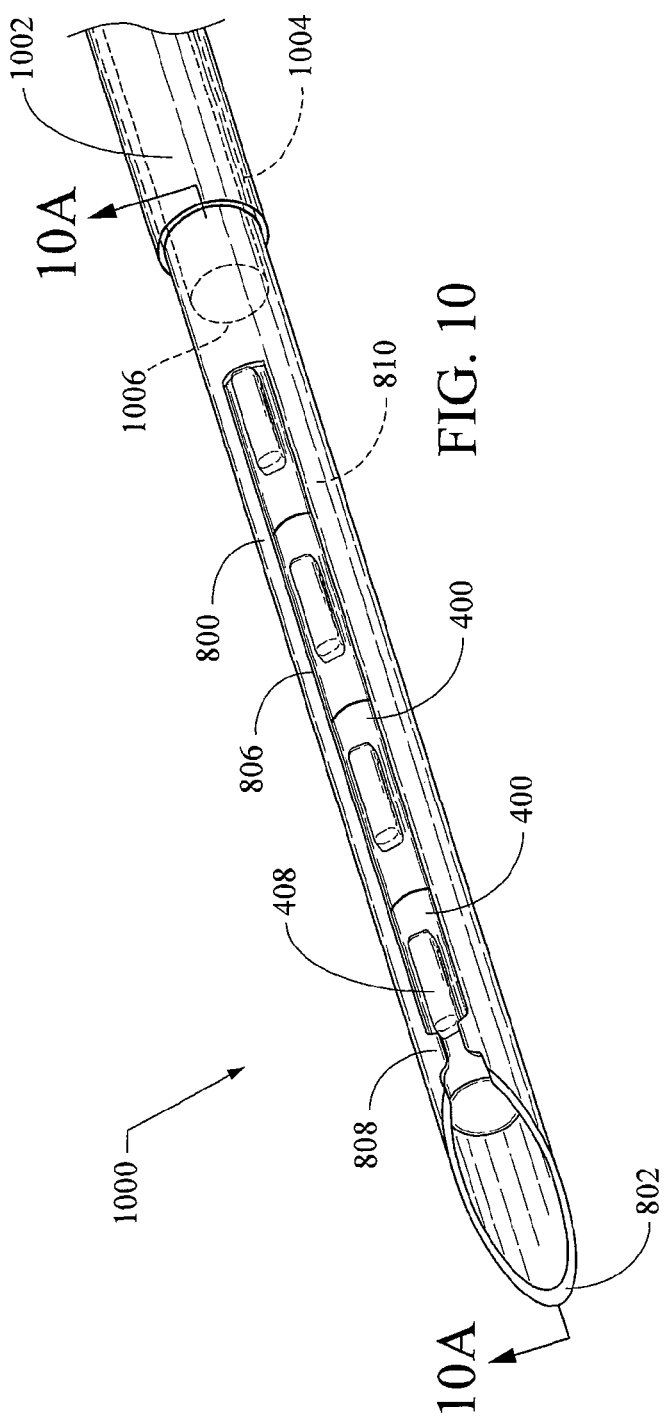
FIGS. 10-10A show, respectively, a top perspective view and a longitudinal section view of a fiducial deployment system.
Figure 10A:
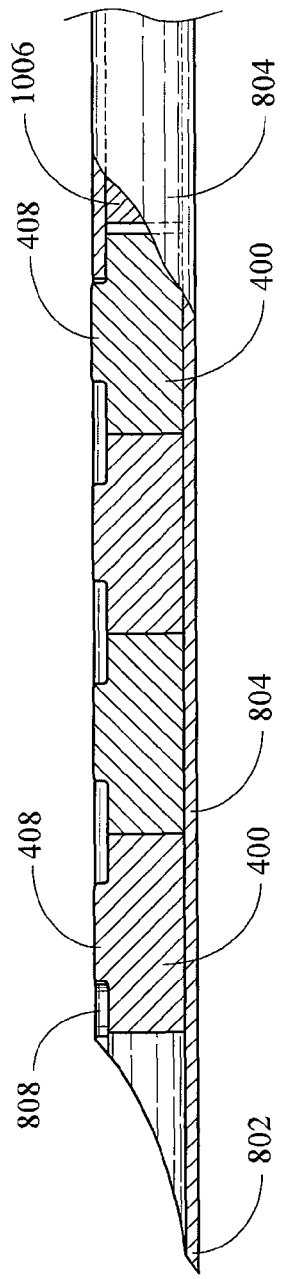

A method of using the fiducial deployment system of FIGS. 10-10A is described with reference to FIGS. 11A-11C, with reference to the structures shown in greater detail in FIGS. 10-10A. In a preferred method of use, an endoscope 1100 is provided, including a working channel 1102. In one preferred method, the endoscope is an EUS endoscope including a distal ultrasound array 1104 configured for ultrasound imaging. The endoscope 1100 preferably also includes a video element 1106 (e.g., CCD, optical camera, or other means for optical visualization). The methods below are described with reference to placing fiducials 400 at the margins of a tumor 1152 of a patient's pancreas 1150.

Figure 11A:
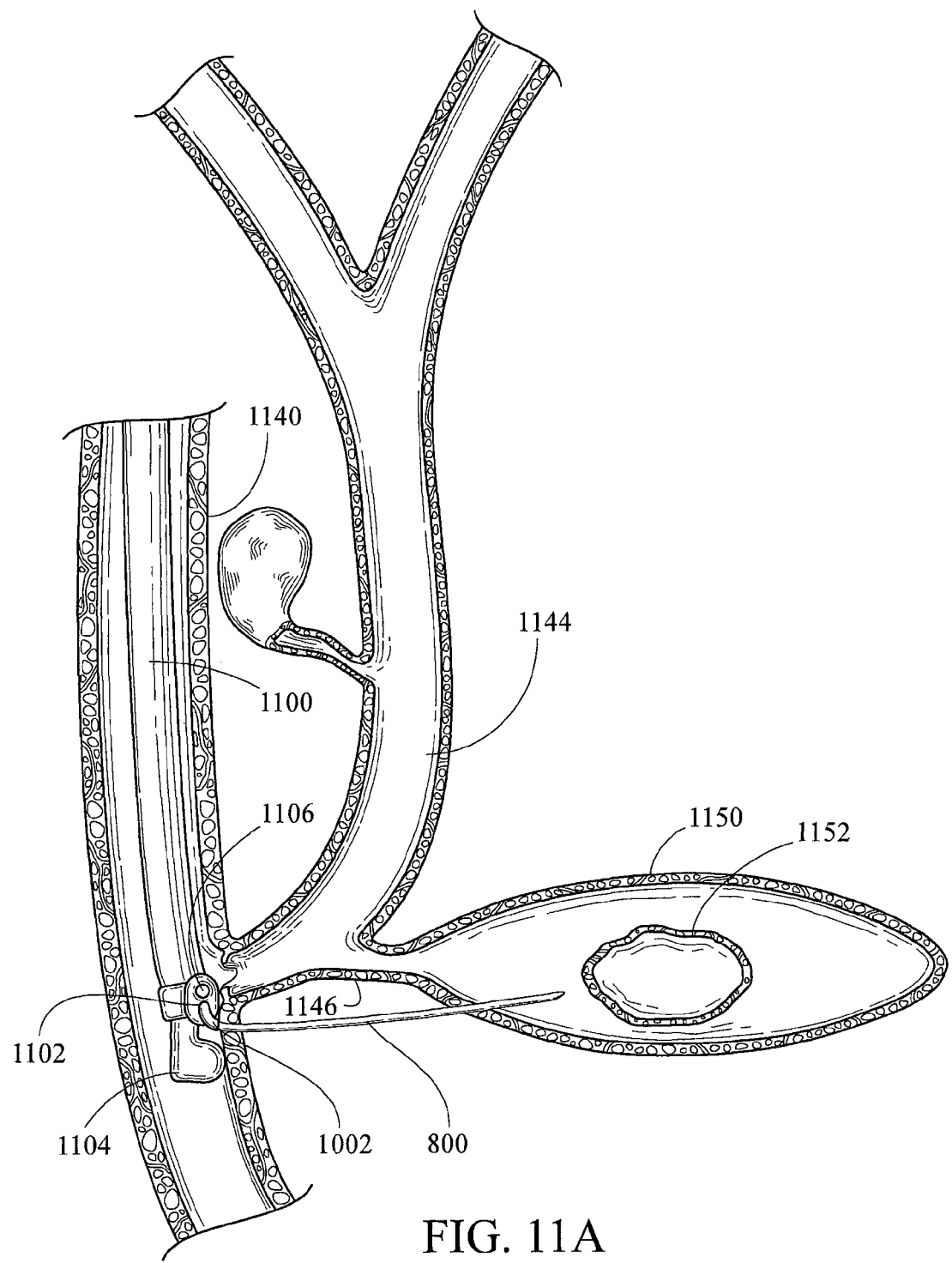
FIGS. 11A-11C show a method of placing fiducials.
Figure 11B:
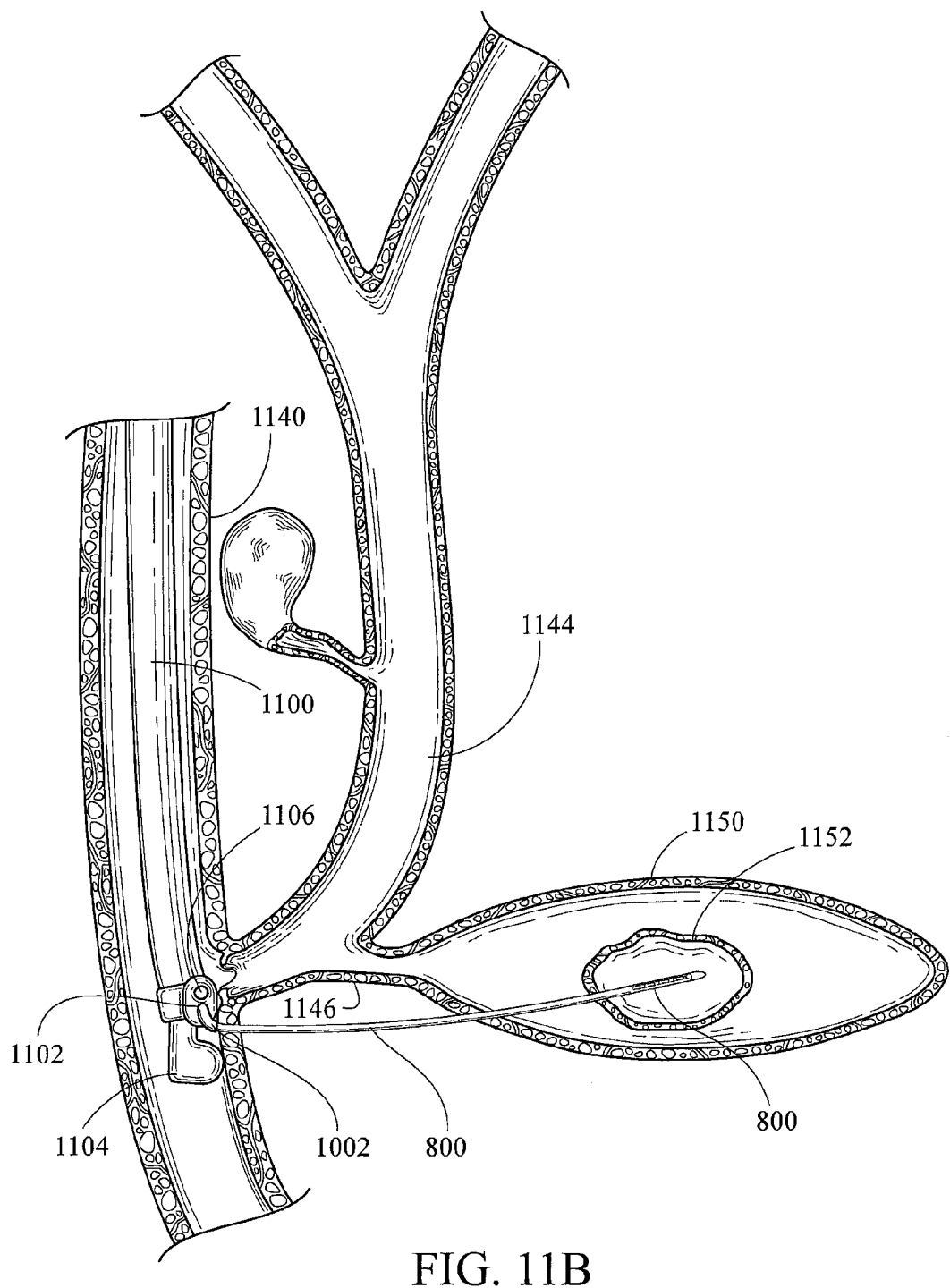
Figure 11C:
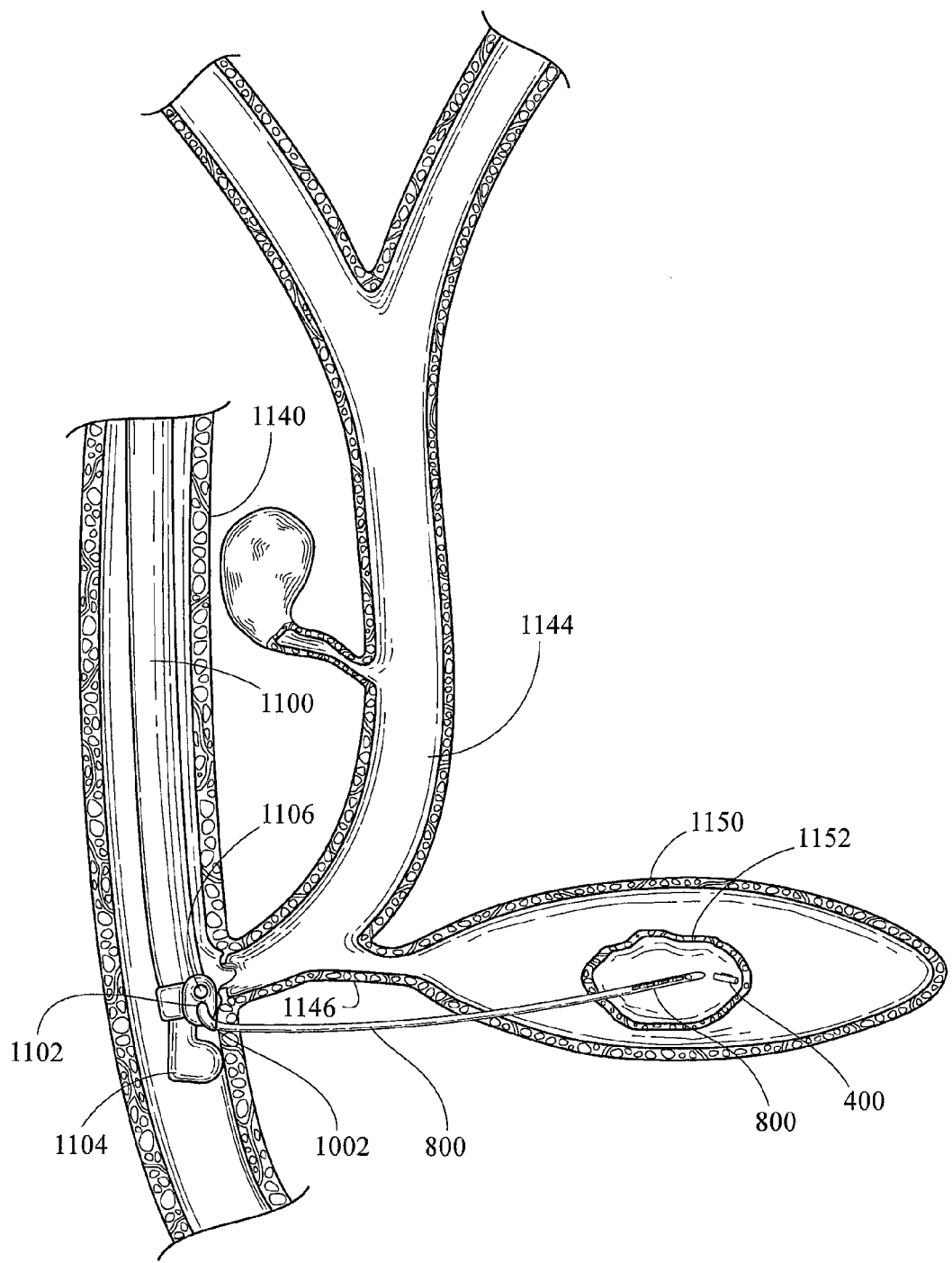

The endoscope 1100 is shown in FIG. 11A as having been directed through a patient's duodenum 1140 until its distal end portion is adjacent the Sphincter of Oddi 1142, which provides access to the common bile duct 1144 from which the pancreatic duct 1146 branches and leads to the pancreas 1150.

As shown in FIG. 11A, the sheath 1002 has been advanced into and through the pancreatic duct 1146 to a location adjacent the tumor 1152. As shown in FIG. 11B, the needle 800 is advanced out of the sheath 1002 and directed to a first target site at a margin of the tumor 1152 (preferably under ultrasound guidance, which can be replaced or verified by fluoroscopy or another visualization technique). Once the distal end 802 of the needle 800 is positioned at the first target, the distal-most fiducial 400 therein is deployed. In one aspect, the deployment may be accomplished by positioning the distal needle end 802 and the fiducial 400 therein at the first target, then retracting the needle 800 while retaining the position of the stylet 1006 such that the fiducial 400 remains in the desired first target position. In another aspect, the deployment may be accomplished by positioning the distal needle end 802 and the fiducial 400 therein adjacent the first target, then holding the needle 800 in position while advancing the stylet 1006 such that the fiducial 400 is advanced into the desired first target position.

As will be appreciated from the structure of the needle 800 and fiducials 400 as shown in FIGS. 10-10A, a user preferably will be able to control advancement/deployment of the fiducials to one at a time. Then the fiducial 400 is in a "ready to deploy" position, its distal protuberance face 408a is engaged against the proximal tab edges 808a. To deploy the fiducial 400, the user must move one of the stylet 1006 or needle 800 relative to the other with sufficient force to advance the protuberance 408 through the tabs 808.

The user preferably will have a tactile sense of resistance as the protuberance 408 passes through the tabs 808, which resistance will decrease immediately as soon as the protuberance clears the tabs. Then the user preferably continues the relative motion of stylet and needle until resistance is again encountered, indicating that the next fiducial behind the distal-most one has met the proximal tab edges 808a.

It is preferred that the fiducials and protuberances on each be proportioned such that complete deployment of a distal-most fiducial includes it substantially clearing the distal needle tip 802 and coincides with the protuberance of the next distal-most fiducial meeting the proximal tab edges 808a. As such, it may be advantageous in some fiducial embodiments to position the protuberance more proximally on the fiducial body such that a fiducial body portion distal of the protuberance is longer than a body portion proximal of the protuberance. (See, for example, the fiducial 200 in FIG. 2A). FIG. 11C shows the fiducial in place, with the needle and sheath both withdrawn away from it.

Next, the user may retract the needle 800 into the sheath 1002 to a sufficient distance allowing it to be re-extended to a second target site, where the procedure described above may be repeated. These steps may be repeated for placement of third, fourth, and further fiducials. As is known in the art, these fiducials may be used for "positive targeting" and/or "negative targeting" of a therapy such as radiation therapy ("positive targeting" indicating "treat here", and "negative targeting" indicating "do not treat here"). The present system presents numerous advantages. For example, consider a patient already undergoing an endoscopy procedure to biopsy a located but undiagnosed tissue mass. The endoscopic biopsy can be taken and a tissue slide prepared immediately. If a diagnosis is made (in conjunction with whatever other data are available and pertinent) that the tissue mass will benefit from a treatment where placement of fiducials is indicated, the physician can immediately deploy fiducials in the manner described above.

Figure 11D:
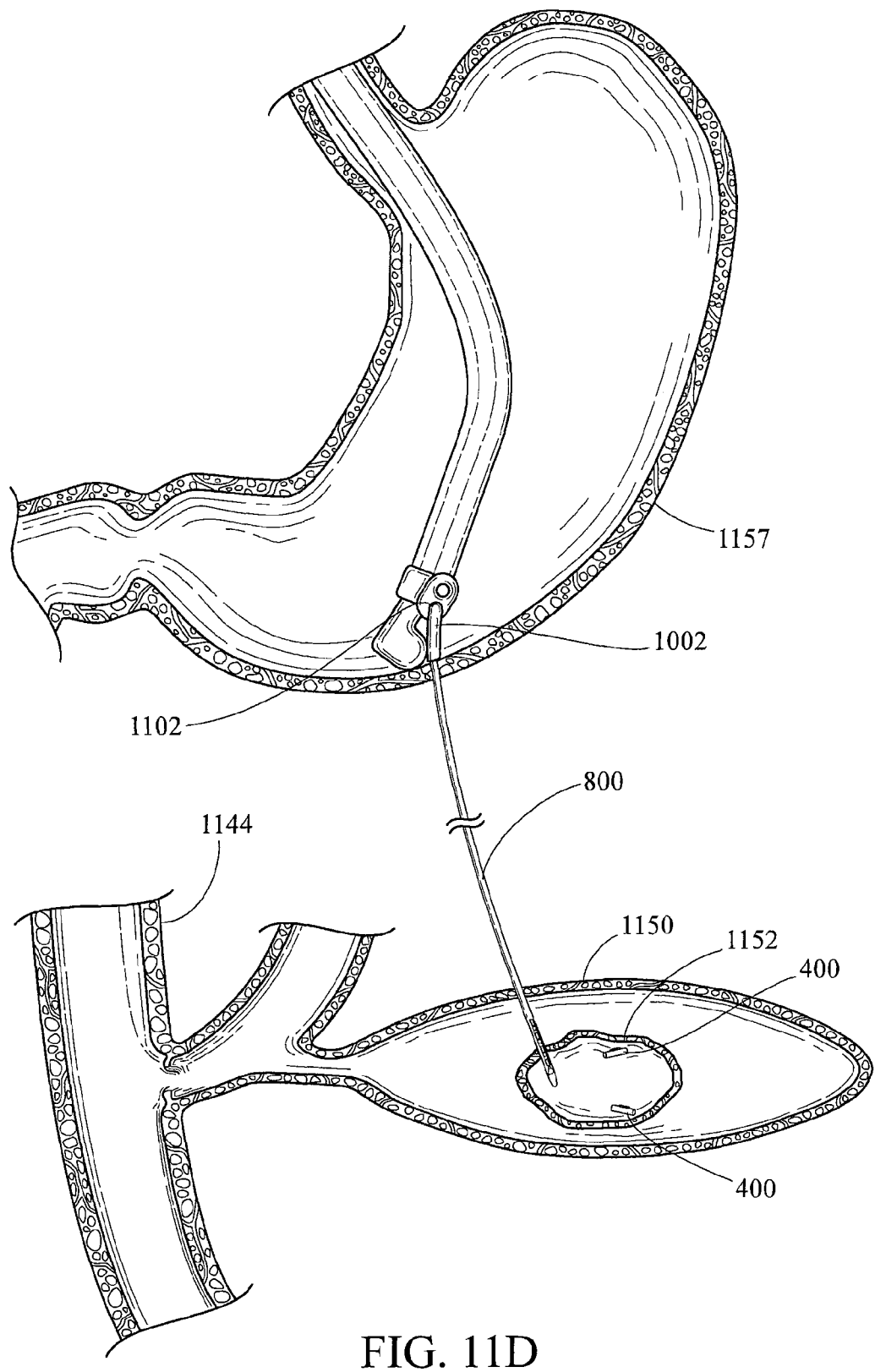
FIGS. 11D-11E show two other methods of placing fiducials.

Preferred method embodiments are described with reference to FIGS. 11D and 11E, each of which will allow use of a larger needle and fiducials. The endoscope 1100 is shown in FIG. 11D as having been directed into a patient's stomach 1157. The sheath 1002 has been advanced until its distal end is adjacent the stomach wall, then the needle 800 has been advanced through the stomach wall, to the pancreas 1150, and into the tumor 1152. This stomach location is sufficiently near the target site (tumor 1152) to provide access to it for the fiducial introduction system. This method preferably is executed under ultrasound visualization using the ultrasound array 1104. Two other fiducials 400 are shown as having been placed in the tumor 1152 already.

Figure 11E:
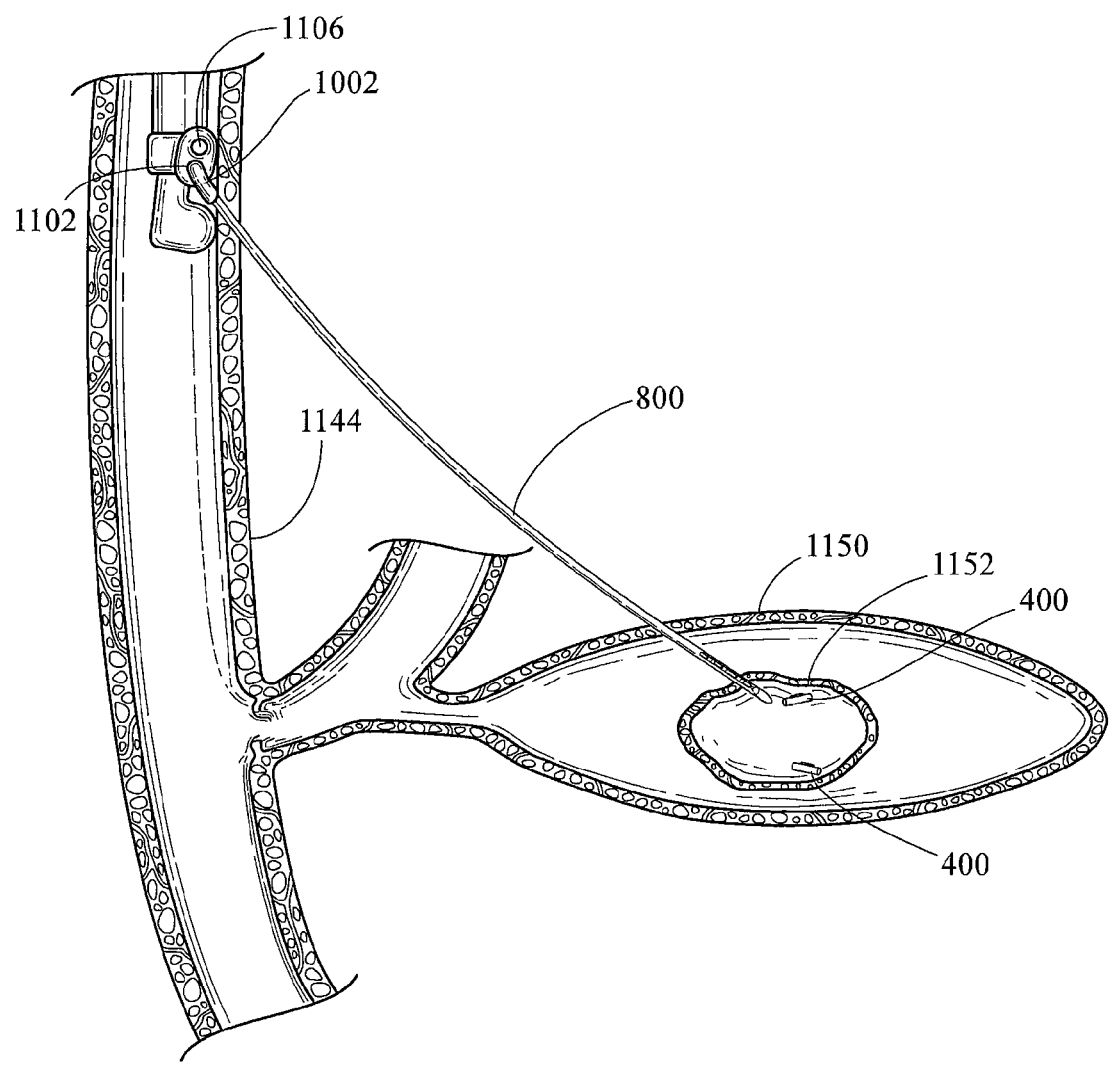

The endoscope 1100 is shown in FIG. 11E as having been directed through a patient's duodenum 1140. The sheath 1002 has been advanced until its distal end is adjacent the duodenal wall, then the needle 800 has been advanced through the duodenal wall, to the pancreas 1150, and into the tumor 1152. This location in the duodenum 1140 is sufficiently near the target site (tumor 1152) to provide access to it for the fiducial introduction system. This method preferably is executed under ultrasound visualization using the ultrasound array 1104. One fiducial 400 is shown as having already been placed in the tumor 1152. The needle 800 has just released another fiducial 400 and been partially retracted.

The ability to complete the method using direct/video and ultrasound imaging with little or no use of fluoroscopy presents an advantage of minimizing the radiation exposure of the patient (who may have to undergo radiation therapies where the total amount of exposure to radiation is desired to be minimized to that which is therapeutically and diagnostically necessary). Advantages of time and expense for the patient, physician and other treating/diagnostic personnel, and the treatment facility are likely as implementation of the present method may prevent all of those entities from having to schedule and conduct a second endoscopic procedure, and/or to extend the initial diagnostic procedure with the time-consuming methods and materials currently available in the prior art as described.

Figure 12A:
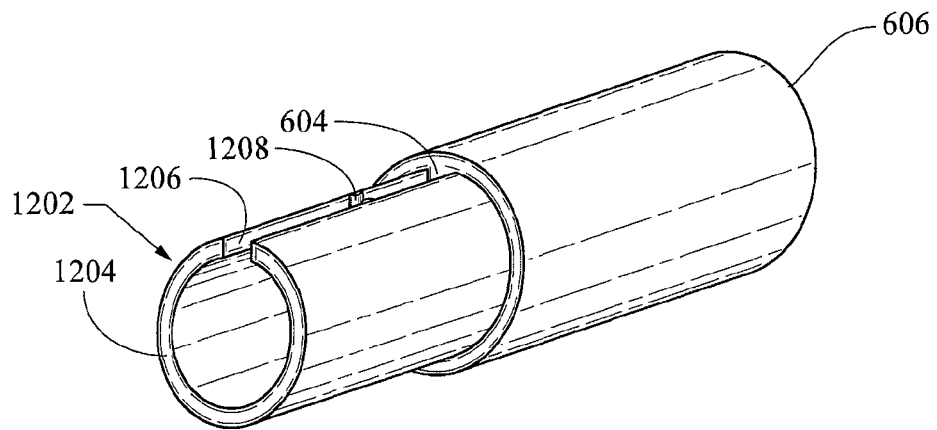
FIGS. 12A-12B show, respectively, top perspective and top plan views of another needle and fiducial embodiment.
Figure 12B:
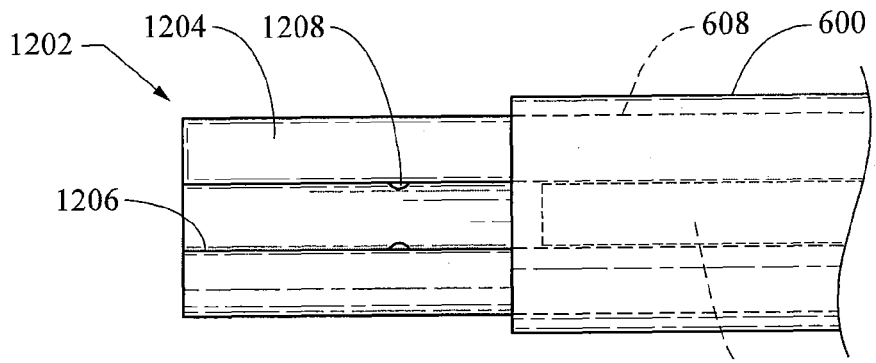

FIGS. 12A and 12B show a needle embodiment 1202 with the fiducial embodiment 600 discussed above with reference to FIGS. 4 and 4A. The needle 1202 includes a cannula body 1204 with a slot 1206 through the cannula body 1204. The fiducial 600 is mounted onto the needle 1202, which may be a smaller needle than is practical for use with fiducial embodiments such as those shown in FIGS. 2A-2E, 3, 5, 6, and 7, as the fiducial 600 includes a portion of its mass disposed around the outside of the needle. The needle cannula body 1204 is disposed through the fiducial needle lumen 608. The fiducial protuberance 604 extends through the needle slot 1206, providing for travel and controlled release as is described above. FIG. 12B shows a top view of the needle 1202, with its slot 1206, and a pair of small detent bumps 1208 on the distal slot edge.

Figure 13:
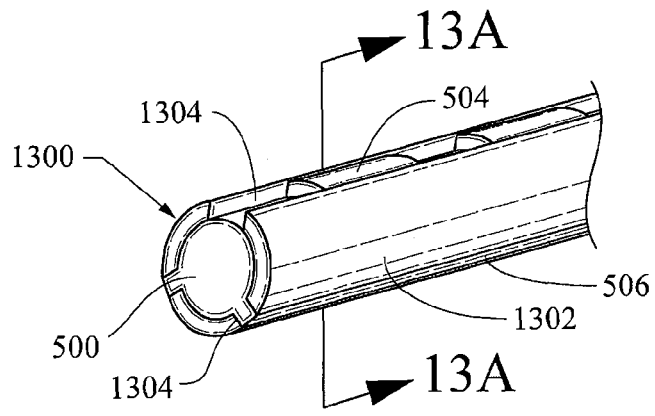
FIGS. 13-13A show, respectively, top perspective and transverse section views of another needle and fiducial embodiment.
Figure 13A:
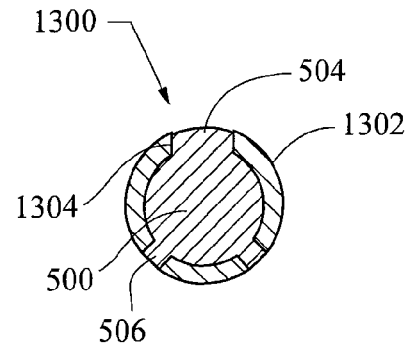

FIG. 13 shows a multi-slot needle 1300 such as might be useful with the fiducial embodiment 500 shown in FIG. 3. The needle 1300 includes a cannular body 1302 with three elongate slots 1304 extending along a distal length. Protuberances such as those (504, 506) shown in FIG. 3 can travel through the slots 1304. Two slots or more than three may be present in other needle embodiments. FIG. 13A shows another view of the needle 1300, including a transverse section view along plane 13A-13A of FIG. 13, which view more clearly illustrates the interaction of the protuberances 504, 506 with the needle slots 1304.

Figure 14:
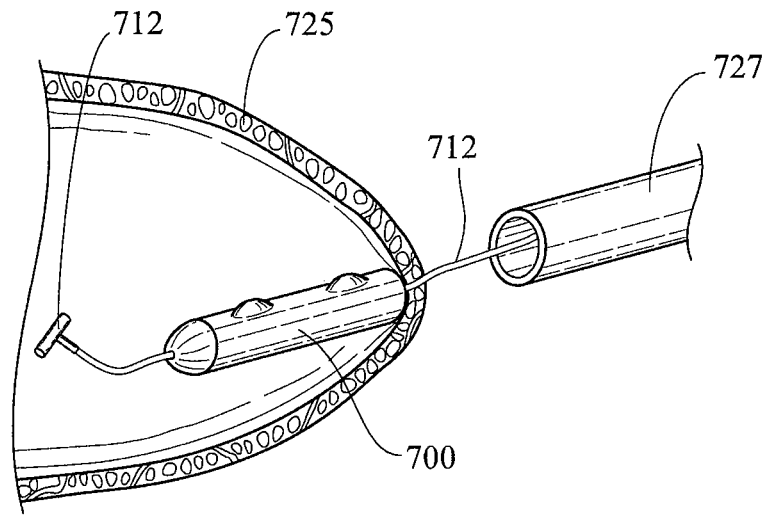
FIG. 14 shows a fiducial-placement method using a t-anchored suture.

FIG. 14 shows placement of a suture-mounted fiducial 700 of the type described above with reference to FIG. 5. In this illustration, a T-anchor-dispensing needle (not shown; these needles are well-known in the art) has been used to deposit a T-anchor 712 into target tissue 725, and the needle withdrawn. A fiducial 700 has been mounted onto the suture 710 and advanced with a pusher catheter 727 into the tissue 725. This structure and method provides a different means for placing a plurality of fiducials, which may or may not include protuberances (which, if present, may allow use of the fiducial 700 with a slotted needle in method operating generally as described above with reference to FIGS. 11A-11C).

Figure 15:
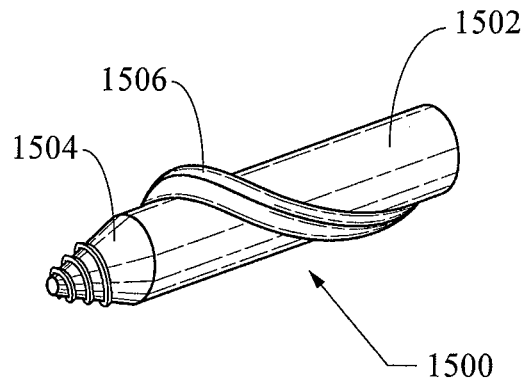
FIGS. 15-15A show, respectively, another fiducial embodiment and another needle embodiment configured for use therewith.
Figure 15A:
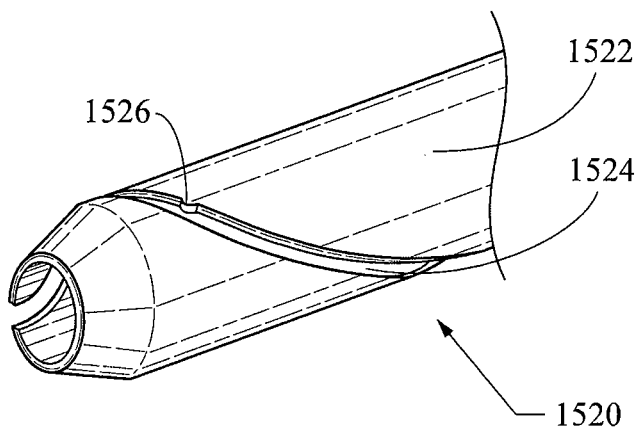

FIGS. 15A and 15B show, respectively, a rifling fiducial 1500 and slotted needle 1520 configured for use with it. The fiducial 1500 includes a generally cylindrical main body 1502 with a conical distal tip 1504 that may include a surface having a helically threaded texture. A protuberance 1506 is partially helically wrapped around the outer circumference of the body 1502. The needle 1520 for this fiducial 1500 is shown in FIG. 15B. It has a generally tubular cannula body 1522 with a helical slot 1524 configured to accommodate the protuberance 1506. The slot 1524 includes a single detent tab 1526 along one edge. As will be appreciated, a fiducial 1500 being advanced through the needle 1520 will riflingly rotate as it exits the needle. This rotation may help it advance more easily in certain tissue types.

Drawings in the figures illustrating various embodiments are not necessarily to scale. Some drawings may have certain details magnified for emphasis, and any different numbers or proportions of parts should not be read as limiting, unless so-designated by one or more claims. Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. For example, a needle and fiducials of the present system may be used percutaneously, including in another minimally invasive surgical procedure, such as a laparoscopic-type procedure, within the scope of the claimed invention. For example, a target site may be a location in or near the gastrointestinal tract (e.g., liver, pancreas) such as those locations that may be accessible by endoscopy (using a minimally invasive endoscope introduced through a natural patient orifice, e.g., mouth, anus, vagina). This includes—more broadly—sites reachable through NOTES (natural orifice translumenal endoscopic surgery) procedures. The present method and device may also be used with other minimally-invasive surgical techniques such as percutaneous endoscopic procedures (e.g., laparoscopic procedures) or percutaneous non-endoscopic procedures, but most preferably is used with less invasive endoscopy procedures. It is therefore intended that the foregoing detailed description be regarded as illustrative rather than limiting. And, it should be understood that the following claims, including all equivalents, are intended to define the spirit and scope of this invention.

The invention claimed is:

1. A fiducial deployment system comprising:
   a needle including a tubular cannula body defining a needle lumen disposed through at least a lengthwise portion of the cannula body and a distal needle end region, the distal end region comprising a distal needle end opening at a distal end of the needle lumen; and
   at least one generally longitudinal needle slot extending radially through at least a thickness portion of the cannula body and open to the needle lumen, where at least one detent structure extends across and within the needle slot near the distal needle end opening;
   a plurality of fiducials disposed in the lumen, each comprising
   a generally columnar body including
      a central fiducial portion slidably disposed in the needle lumen; and
      at least one side protuberance projecting into the needle slot so as to engage a proximal surface of the at least one detent; and
   a stylet extending through a portion of the needle lumen and configured to advance each of the plurality of fiducials past the at least one detent and out of the distal needle end opening in a controlled, one at a time, serial manner.

2. The fiducial deployment system of claim 1, where the at least one protuberance of at least one of the plurality of fiducials comprises a plurality of protuberances.

3. The fiducial deployment system of claim 2, where more than one of the plurality of protuberances are generally longitudinally aligned with each other.

4. The fiducial deployment system of claim 1, where each fiducial includes a proximal end and a distal fiducial end, where the proximal end of at least one of the fiducials is immediately adjacent the distal end of another of the fiducials, and where a longitudinal length of each fiducial is greater than a longitudinal length of its protuberance.

5. The fiducial deployment system of claim 1, where the at least one generally longitudinal needle slot comprises a plurality of needle slots including a first needle slot and a second needle slot.

6. The fiducial deployment system of claim 5, where the at least one protuberance of at least one of the plurality of fiducials comprises a plurality of protuberances including a first protuberance and a second protuberance, and where the first protuberance at least partially occupies the first slot and the second protuberance at least partially occupies the second slot.

7. The fiducial deployment system of claim 1, where a lengthwise gap between the protuberances of the fiducials is at least as long as the at least one detent.

8. The fiducial deployment system of claim 1, where the central fiducial portion comprises a generally non-cylindrical portion.

9. The fiducial deployment system of claim 1, where at least one of the plurality of fiducials comprises at least one echogenic surface.

10. The fiducial deployment system of claim 1, further comprising being at least partially disposed through a working channel of an endoscope.

11. A method of placing a fiducial into a patient body, the method comprising the steps of providing the fiducial deployment system of claim 10;
   directing a distal end of the endoscope to a location near a first target site in a patient body;
   directing the distal needle end to the first target site; and
   deploying at least a first one of the plurality of fiducials by performing an action selected from
      (i) advancing the stylet distally through the needle lumen to push the at least one fiducial past the at least one detent surface and into the first target site;
      (ii) retracting the needle proximally relative to the stylet such that the at least one detent surface is pulled proximally past the fiducial protuberance and the first fiducial is released out of the needle lumen into the first target site; and
      (iii) a combination thereof.

12. The method of claim 11, further comprising the steps of:
   withdrawing the needle proximally from the target site and directing the needle to a second target site.

13. The method of claim 11, where the step of directing the distal needle end to the first target site includes using ultrasound visualization to determine location of the needle by visualization of at least one of the plurality of fiducials in the needle lumen.

14. The method of claim 12, where the relative movement of the stylet and needle to each other during the step of deploying at least a first fiducial is continued until the protuberance of a second fiducial contacts the at least one detent proximal surface.

15. A fiducial configured for deployment in a patient body to be used for demarcating an internal body site, the fiducial comprising:
   a generally columnar body including
      a proximal fiducial end;
      a distal fiducial end; and
      a longitudinally central fiducial portion including at least one side protuberance projecting beyond the outer fiducial diameter, the side protuberance configured for aligning and retaining the fiducial in a lumen of a slotted needle;
   further comprising a central lumen configured for passage of the fiducial along a suture, and a suture disposed through the central lumen.

* * * * *